US008658011B2

(12) United States Patent
Hoashi et al.

(10) Patent No.: US 8,658,011 B2
(45) Date of Patent: Feb. 25, 2014

(54) GLUCOSE SENSOR

(71) Applicant: ARKRAY, Inc., Kyoto (JP)

(72) Inventors: Shogo Hoashi, Kyoto (JP); Takehiro Yamaguchi, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 0 days.

(21) Appl. No.: 13/625,222

(22) Filed: Sep. 24, 2012

(65) Prior Publication Data

US 2013/0075276 A1 Mar. 28, 2013

(30) Foreign Application Priority Data

Sep. 26, 2011 (JP) ................................. 2011-209443
Sep. 4, 2012 (JP) ................................. 2012-194188

(51) Int. Cl.
*G01N 27/327* (2006.01)
(52) U.S. Cl.
USPC .......................... 204/403.01; 205/792; 435/14
(58) Field of Classification Search
USPC ............. 204/403.01–403.15; 205/777.5, 778, 205/792; 600/345–348; 435/4–40.52; 436/62–71, 500–548; 422/68.1–98
See application file for complete search history.

(56) References Cited

U.S. PATENT DOCUMENTS

| 2004/0245121 A1 | 12/2004 | Nagakawa et al. |
| 2006/0063217 A1 | 3/2006 | Omura et al. |
| 2007/0034512 A1 | 2/2007 | Yamaoka et al. |
| 2007/0295616 A1* | 12/2007 | Harding et al. ............ 205/777.5 |
| 2008/0014612 A1 | 1/2008 | Tsuji et al. |
| 2008/0220460 A1 | 9/2008 | Kawaminami et al. |
| 2008/0248514 A1 | 10/2008 | Inamori et al. |
| 2009/0259024 A1 | 10/2009 | Tsuji et al. |
| 2011/0033880 A1 | 2/2011 | Yada et al. |

FOREIGN PATENT DOCUMENTS

| JP | 2008-035748 A | 2/2008 |
| JP | 4179384 B2 | 11/2008 |
| JP | 4292486 B2 | 7/2009 |
| JP | 2009-225801 A | 10/2009 |
| JP | 4348563 B2 | 10/2009 |
| JP | 4381369 B2 | 12/2009 |
| JP | 4381463 B2 | 12/2009 |
| JP | 4385219 B2 | 12/2009 |
| JP | 2011-139677 A | 7/2011 |
| WO | 03/025558 A1 | 3/2003 |
| WO | 2004/058958 A1 | 7/2004 |
| WO | 2005/043146 A1 | 5/2005 |
| WO | 2009/119728 A1 | 10/2009 |

* cited by examiner

*Primary Examiner* — J. Christopher Ball
(74) *Attorney, Agent, or Firm* — Fox Rothschild LLP (57) ABSTRACT

Provided is a glucose sensor that is capable of measuring a glucose concentration even in the case where *Aspergillus oryzae* type FAD-GDH (flavin adenine dinucleotide-glucose dehydrogenase) and a ruthenium compound are used in combination. The glucose sensor includes an insulative substrate, an electrode system having a working electrode and a counter electrode provided on the substrate, and a reagent layer provided on the electrode system, wherein the reagent layer contains *Aspergillus oryzae* type FAD-GDH, a ruthenium compound, and PMS (phenazine methosulfate).

11 Claims, 4 Drawing Sheets

GLUCOSE SENSOR

TECHNICAL FIELD

The present disclosure relates to a glucose sensor that contains *Aspergillus oryzae* type FAD-GDH (flavin adenine dinucleotide-glucose dehyrogenase) and a ruthenium compound.

BACKGROUND ART

As a GDH (glucose dehydrogenase) used in methods for determining a quantity of glucose with use of glucose oxidation enzymes of various types, FAD-GDH derived from *Aspergillus oryzae* is disclosed in JP429248613. Further, JP4348563B discloses wild type FAD-GDH of *Aspergillus oryzae* and modifications of the same have a low effect on maltose and galactose and a high substrate specificity with respect to glucose.

WO2005/043146 discloses a biosensor comprising an electrode system having a working electrode and a counter electrode formed on an electrically insulative substrate, a reagent layer containing an oxidation-reduction enzyme such as GDH or GOD (glucose oxidase), and a mediator. WO2003/025558 disclosure a ferricyanide compound, a ruthenium compound, or the like used as the mediator.

SUMMARY

Various studies have been conventionally made about a method for determining, a quantity of glucose with use of various types of glucose oxidation enzymes, which are commercially available. The principle for the method of determining a quantity of glucose with use of a glucose oxidation enzyme is based on the mechanism in which a coenzyme for the oxidase is reduced at the same time when glucose is oxidized by the oxidase. More specifically, the methods can be roughly classified as the method of measuring an absorbance of the reduced coenzyme or an electron transfer substance (colorimetric method), and as the method of measuring an electric, current generated by an oxidation-reduction reaction (electrode method). Particularly in recent years, the electrode method has been mainly used for a simple glucose sensor that diabetic patients use for determining his/her blood glucose routinely.

The use of GOD as the glucose oxidation enzyme has a long history. In the case where GOD is applied to the electrode method, however, there has been a problem that the dissolved oxygen level in a sample affects the determined quantity, since GOD can utilize molecular oxygen as an electron acceptor. To solve this problem, GDH, which cannot utilize molecular oxygen as an electron acceptor, came to be used often.

GDHs are roughly classified into the following three types: those which work along with pyrroloquinoline quinone (PQQ) as a coenzyme (PQQ-GDH) those which work along with flavin adenine dinucleotide (FAD) as a coenzyme (FAD-GDH); and those which work along with nicotinamide adenine dinucleotide (NAD) or nicotine adenine dinucleotide phosphate (NADP) as a coenzyme (NADP-GDH). Regarding GDH its substrate specificity arose as a problem often. More specifically, it has been known that GDH works on, not only glucose, but also other substances such as maltose and galactose, as substrates. As a solution to this problem of substrate specificity, FAD-GDH derived from *Aspergillus oryzae* was identified. The wild type FAD-GDH of *Aspergillus oryzae* and modifications of the same have a low reactivity on maltose and galactose and a high substrate specificity with respect to glucose. Therefore, the of these FAD-GDHs in glucose sensors has been proposed.

Biosensors such as glucose sensors generally have a configuration in which an electrode system having a working electrode and a counter electrode is formed on an electrically insulative substrate, and a reagent layer containing an oxidation-reduction enzyme such as GDH or GOD as well as a mediator is provided on the electrode system. As the mediator, a ferricyanide compound, a ruthenium compound, or the like is used.

Wild type FAD-GDH of *Aspergillus oryzae* and modifications of the same (hereinafter referred to as "*Aspergillus oryzae* type FAD-GDH" as well) ma be combined with a mediator such as a ferricyanide compound or the like (except for a ruthenium compound), so that a glucose sensor for determining a glucose concentration can be produced. The ruthenium compound also may be combined with GDH or GOD other than the *Aspergillus oryzae* type FAD-GDH, so that a glucose sensor for determining a glucose concentration can be produced. However, a glucose sensor obtained by combining *Aspergillus oryzae* type FAD-GDH and a ruthenium compound cannot determine a glucose concentration.

Then, this disclosure provides, as one aspect, a glucose sensor that is capable of measuring a glucose concentration even in the case where *Aspergillus oryzae* type FAD-GDH and a ruthenium compound are used in combination The present disclosure, as one aspect, relates to a glucose sensor that includes an insulative substrate, an electrode system having a working electrode and a counter electrode provided on the substrate, and a reagent layer provided on the electrode system, wherein the reagent layer contains *Aspergillus oryzae* type FAD-GDH, a ruthenium compound, and phenazine methosulfate (PMS).

The present disclosure, as another aspect, relates to a glucose concentration measurement method for measuring a concentration of glucose in a sample, by using an electrode system having a working electrode and a counter electrode provided on an insulative substrate, glucose dehydrogenase, and a mediator, the method including: bringing the sample and *Aspergillus oryzae* type FAD-GDH into contact with each other; and electrochemically measuring a reaction between the glucose in the sample and the *Aspergillus oryzae* type FAD-GDH via PMS and a ruthenium compound.

The present disclosure, as another aspect, relates to a method for producing a glucose sensor, the method including forming a reagent layer containing *Aspergillus oryzae* type FAD-GDH ruthenium compound, and PMS on an electrode system provided on an insulative substrate, the electrode system having a working electrode and a counter electrode.

The present disclosure, as another aspect, relates to a glucose concentration measurement system for measuring a concentration of glucose in a sample, the system including: the glucose sensor of the present disclosure; a means for applying a voltage to the electrode system in the glucose sensor; and a means for measuring an electric current in the electrode system.

According to the present disclosure as an aspect; a glucose sensor can be provided that is capable of measuring a concentration of glucose by using a combination of *Aspergillus oryzae* type FAD-GDH having a low reactivity with maltose and galactose and a high substrate specificity with respect to glucose, and a ruthenium compound as a mediator.

DETAILED DESCRIPTION

In the case in which a glucose sensor is produced with use of a ruthenium compound alone as a mediator for *Aspergillus oryzae* type FAD-GDH, an electric current value depending on a glucose concentration in a sample cannot be obtained, and the glucose concentration cannot be measured. The present disclosure, in one aspect, is based on the surprising discovery that a glucose sensor having the above-described configuration becomes capable of measuring a glucose concentration if PMS is used as a mediator in addition to a ruthenium compound.

Figure 1:
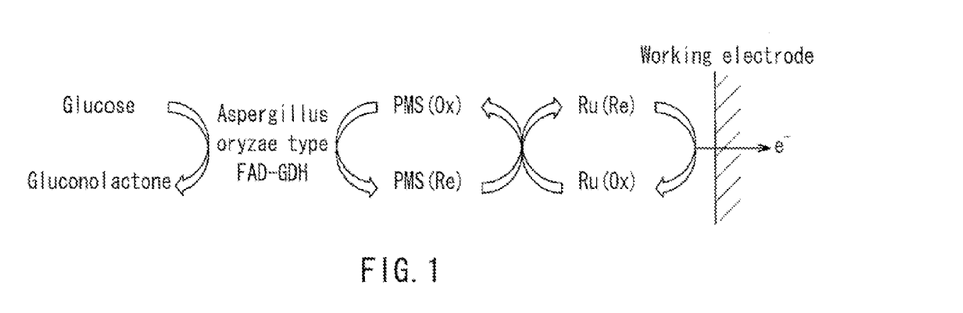
FIG. 1 shows an electrochemical sensing scheme with respect to glucose by an *Aspergillus oryzae* type FAD-GDH

A scheme of electrochemical measurement of a reaction between *Aspergillus oryzae* type FAD-GDH and glucose is shown in FIG. 1. First, electrons provided by a reaction of *Aspergillus oryzae* type FAD-GDH with glucose are supplied to PMS (oxidized type) as the first mediator, thereby reducing PMS. Glucose is transferred to Gluconolactone. Next, electrons are supplied from the reduced type PMS to the ruthenium compound (Ru) (oxidized type) as the second mediator, therein, reducing the ruthenium compound. Then, electrons are supplied from the reduced type ruthenium compound to an electrode (working electrode), and are measured as an electric current value. In the interpretation of the present disclosure, however, the present disclosure is not limited to this mechanism.

[*Aspergillus oryzae* type FAD-GFH]

In the present specification, "FAD-GDH" means flavin adenine dinucleotide-dependent glucose dehydrogenase, or flavin adenine dinucleotide-binding glucose dehydrogenase. In the present specification, "*Aspergillus oryzae* type FAD-GDH" means wild type FAD-GDH of *Aspergillus oryzae* and/or modifications of the same, and includes both the wild type and modifications thereof, unless otherwise provided. In the present specification, the "*Aspergillus oryzae* type FAD-GDH" preferably means FAD-GDH that has a low effect on maltose and galactose and a high substrate specificity with respect to glucose, as compared with conventionally known non-FAD-binding GDH.

An exemplary wild type FAD-GDH of *Aspergillus oryzae* is a known protein having an amino acid sequence set forth in the Sequence Listing as SEQ ID NO: 1, in one or a plurality of embodiments.

In the present specification, "modifications of the wild type FAD-GDH of *Aspergillus oryzae*" means modifications of the wild type FAD-GDH, each modification haying a sequence obtained by altering, adding or deleting a single amino acid residue or a small percentage of amino acid residues in an amino acid sequence of the wild type FAD-GDH and retaining a flavin adenine dinucleotide-dependent glucose dehydrogenase activity. The modifications, as is the case with the wild type, preferably have a low effect on maltose and galactose, and a high substrate specificity with respect to glucose.

The number of altered, added, or deleted amino acid residues is, for example, 1, 2, 3, 4, or 5, preferably 1 to 3, and more preferably to 2.

A commercially available *Aspergillus oryzae* type FAD-GDH can be used as the *Aspergillus oryzae* type FAD-GDH in the present specification. In one or a plurality of embodiments. *Aspergillus oryzae* type FAD-GDH manufactured by TOYOBO Co., Ltd., which was used in vies, can be used, for example. Examples of embodiments of the *Aspergillus oryzae* type FAD-GDH that may be used in the present disclosure include those described in Patent Documents 1 and 2.

In the present specification, examples of the *Aspergillus oryzae* type FAD-GDH may include a recombinant version that is obtained by adding a tag sequence or a peptide sequence for enzyme purification, and/or a cleaved remnant of the sequence, to an N-terminus or a C-terminus of an amino acid sequence, and that has a flavin adenine dinucleotide-dependent glucose dehydrogenase activity, in one or a plurality of embodiments.

The content of *Aspergillus oryzae* type FAD-GDH per one glucose sensor may be an amount of the same provided in a conventional glucose sensor or a glucose sensor to be developed in future, in one or a plurality of embodiments. The foregoing content is preferably 0.5 to 10 U, more preferably 1 to 6 U, and further preferably 1 to 4 U, from the viewpoint of the productivity (cost) and the maintenance of detection sensitivity, it should be noted that "U" referred to in the present specification is an enzyme unit, and "1 U" is are amount of *Aspergillus oryzae* type FAD-GDH that oxidizes 1 mmol of glucose at 37° C. in 1 minute.

It should be noted that the "content per one glucose sensor" in the present specification refers to an amount used in a glucose sensor having one electrode system having a working electrode and a counter electrode in one or a plurality of embodiments. The foregoing phrase refers to an amount contained in a reagent layer provided on one electrode system in (briber one or a plurality of other embodiments. The foregoing phrase refits to an amount provided so that it is contained in a reaction system when a reagent is added (when it is used) in further one or a plurality of other embodiments. A glucose sensor referred to in the phrase of the "content per one glucose sensor" in the present specification refers to a glucose sensor in a conventional size as described below that is used or will be used in commercial glucose sensor products or the like with respect to a blood sample, in one or a plurality of embodiments. The foregoing size is a size in the case where a blood sample added thereto is 0.2 to 1.0 µL, or 0.2 to 0.4 µL in one or a plurality of embodiments, or alternatively, it is a size in the case where a capacity of a reaction system that is formed by a blood sample in contact with a reagent layer is 0.2 to 1.0 µL, or 0.2 to 0.4 µL in one or a plurality of embodiments. Therefore, regarding, the "content per one glucose sensor", the range thereof disclosed in the present specification can be appropriately adjusted depending on the number of electrodes, and/or a capacity of a sample or a reaction system, in one or a plurality of embodiments.

[Ruthenium Compound]

As the "ruthenium compound" mentioned in the specification, a ruthenium compound used as a mediator in a conventional glucose sensor or biosensor or those to be developed can be used, in one or a plurality of embodiments. The ruthenium compound is preferably a ruthenium compound that can be present as an oxidized-type ruthenium complex in a reaction system. Regarding the ruthenium complex, the type of a ligand of the ruthenium compound is not limited particularly as long as the ruthenium compound functions as a mediator (electron transmitter), but an oxidized type expressed as the following chemical formula is preferably used.

Examples of X in the above-described chemical formula include $NH_3$, halogen ions, CN, pyridine, nicotine amide, and $H_2O$, among which $NH_3$ or halogen ions (e.g., $Cl^-$, $F^-$, $Br^-$, $I^-$) are preferably used. $n^+$ in the above-described chemical formula represents the valence of the oxidized type ruthenium (III) complex determined depending on the type of X.

The content of the ruthenium compound per one glucose sensor may be an amount of the same provided in a conventional glucose sensor or a glucose sensor to be developed in future, in one or a plurality of embodiments. The content of the ruthenium compound is preferably 5 to 50 μg, more preferably 10 to 40 μg, and further preferably 15 to 25 μg, from the viewpoint of the productivity (cost) and the detection sensitivity.

[PMS]

In the present specification, "PMS" refers to phenazine methosulfate and derivatives thereof. As the PMS, 1-methoxy-5-methylphenazinium methyl sulfate (1-methoxy PMS) is preferable from the viewpoint of the reagent stability.

The content of PMS per one glucose sensor is preferably 40 to 900 pmol, more preferably 50 to 500 pmol, and further preferably 100 to 300 pmol, from the viewpoint of the productivity (cost) and the detection sensitivity.

In the case where the content of PMS per one glucose sensor is 200 pmol, the content of *Aspergillus oryzae* type FAD-GDH is 1 to 6 U, or 1 to 4 U, in one or a plurality of embodiments, and the content of ruthenium compound is 10 to 40 μg, or 15 to 25 μg, in one or a plurality of embodiments.

[Other Components Contained in the Reagent Layer]

The reagent layer in one or a plurality of embodiments may contain a layered inorganic compound, a surfactant, a buffering agent, etc., from the viewpoint of improving the measurement sensitivity. As the layered inorganic compound, any of those used in conventional glucose sensors or glucose sensors to be developed can be used, in one or a plurality of embodiments. From the viewpoint described above, the layered inorganic compound is preferably any of swelling clay minerals having ion exchange capacity; more preferably any of bentonite, smectite, vermiculite, synthesized fluorine mica and the like, and further more preferably any of the following: synthetic smectites such as synthetic hectorite, synthetic saponite and the like; swelling synthetic micas such as synthetic fluorine mica; and synthetic micas such as Na type mica (natural mica is normally a non-swell mg day mineral). Such a layered inorganic compound may be used alone, or two or more of the same may be used in combination.

As the surfactant, any of those which can be used in a conventional glucose sensor or a glucose sensor to be developed in future can be used, and the surfactant is not limited particularly. Any of nonionic, anionic, cationic, and ampholytic surfactants can be used appropriately, in one or a plurality of embodiments. Among these, ampholytic surfactants are preferred, from the viewpoint of improving the measurement sensitivity. Examples of the ampholytic surfactants include carboxybetaine, sulfobetaine and phosphobetaine, among which sulfobetaine is preferred, from the same viewpoint as that described above. Examples of sulfobetaine include CHAPS (3-[(3-cholamidopropyl)dimethylammonium]propanesulfonate), CHAPSO (3-[(3-cholamidopropyl)dimethylammonium]-2-hydroxy-1-propanesulfonate), and alkylhydroxysulfobetaine. Among these, CHAPS is preferred from the same viewpoint.

As the buffering agent, any of those which can be used in a conventional glucose sensor or a glucose sensor to be developed, in future can be used and is not limited particularly. In one or a plurality of embodiments, however, an amine-based buffering agent and a buffering agent having a carboxyl group are preferred from the viewpoint of improving the measurement sensitivity. Examples of the amine-based buffering agent preferably used include, from the same viewpoint, Tris (tris(hydroxymethyl)-aminomethane), ACES (N-(2-Acetamido)-2-aminoethanesulfonic acid), CHES (N-Cyclohexyl-2-aminoethanesulfonic acid), CAPSO, TAPS (N-Tris(hydroxymethyl)methyl-3-aminopropanesulfonic acid), CAPS (N-Cyclohexyl-3-aminopropanesulfonic acid), Bis-Tris (Bis (2-hydroxyethyl)iminotris(hydroxymethyl)methane), TAPSO (2-Hydroxy-N-tris(hydroxymethyl)methyl-3-aminopropanesulfonic), TES (N-Tris(hydroxymethyl)methyl-2-aminoethanesulfonic acid), Tricine, and ADA (N-(2-Acetamido)iminodiacetic acid). Among these, ACES and Tris are preferred, among which ACES is more preferred. Preferably used as the buffering agent having the carboxyl group is any of an acetic acid-sodium acetate buffering agent, to malic acid-sodium acetate buffering agent, a maronic acid-sodium acetate boning agent, and a succinic acid-sodium acetate buffering agent, from the same viewpoint, among which a succinic acid-sodium acetate buffering agent is further preferable. One of these buffering agents may be used alone, or two or more of the same may be used in combination.

The above-described reagent layer may have a single layer structure in which all of reagents are contained, or may be a laminar structure composed of a plurality of layers, in one or a plurality of embodiments. In one or a plurality of embodiments, the reagent layer may have a laminar configuration in which an inorganic gel layer containing the aforementioned layered inorganic compound is formed, and an enzyme layer containing *Aspergillus oryzae* type FAD-GDH is formed on the inorganic gel layer. The reagent layer in a glucose sensor is preferably provided in a dried state on an electrode system, from the viewpoint of the storage stability.

[Sample]

A sample to be measured by a glucose sensor of the present disclosure and a glucose measurement method of the present disclosure may be a biological sample such as blood, body fluid, urine, etc., or may be another liquid sample, in one or a plurality of embodiments.

[Glucose Sensor]

A glucose sensor of the present disclosure has a configuration having an insulative substrate, an electrode system having as working electrode and a counter electrode provided on the substrate, and a reagent layer provided on the electrode system. The electrode system may have a reference electrode in one or a plurality of embodiments. As the electrodes, those which are used in a conventional glucose sensor or a glucose sensor to be developed in future can be used, and the electrodes are not limited particularly. In one or a plurality of embodiments, however, carbon electrodes may be used as the working electrode and the counter electrode, or alternatively, metal electrodes made of platinum, gold, silver, nickel palladium, or the like may be used. The reference electrode is not limited particularly, and a reference electrode that is generally used in electrochemical experiments or a reference electrode to be developed in future can be used. In one or a plurality of embodiments, however, a saturated calomel electrode, silver-silver chloride, etc., can be used, for example. As to a method for forming electrodes on an insulative substrate, a printing technique such as photolithography, screen printing: gravure printing, or flexo printing can be used for forming electrodes on the substrate, in one or a plurality of embodiments. As to a material for the insulative substrate, materials that can be used in a conventional glucose sensor or in a glucose sensor to be developed in future can be used, and are not limited particularly. Examples of the material for the insulative substrate, in one or a plurality of embodiments include silicon, glass, glass epoxy, ceramic, polyethylene terephthalate (PET), polystyrene, polymethacrylate, polypropylene, acrylic resin, polyvinyl chloride, polyethylene, polypropylene, polyester, and polyimide.

Figure 3A:
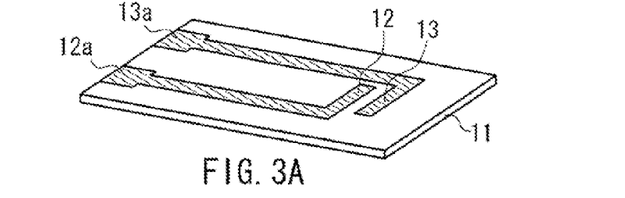
FIGS. 3A-3F are schematic diagrams illustrating an example of a glucose sensor configuration and a method for producing the same.
Figure 3B:
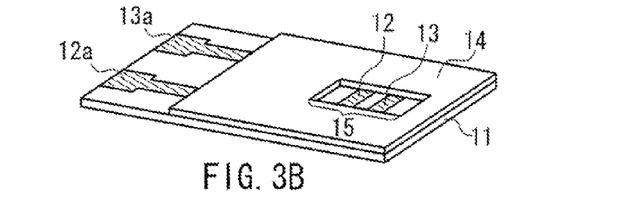
Figure 3C:
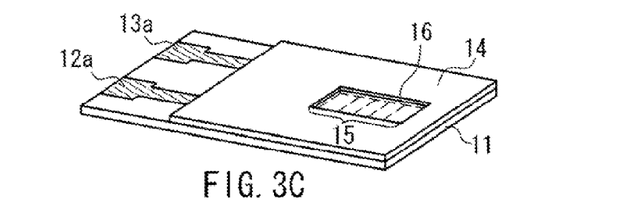
Figure 3D:
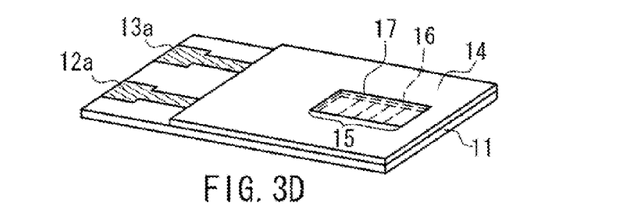
Figure 3E:
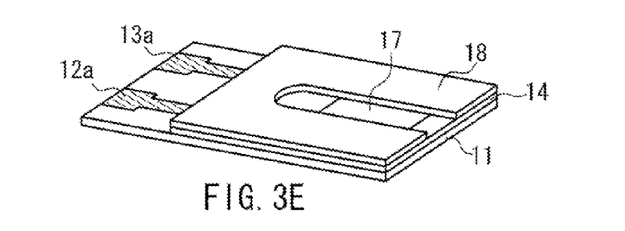

One embodiment of a glucose sensor of the present disclosure is explained with reference to FIGS. 3 and 4. FIGS. 3A to 3F are perspective views showing a series of steps for producing the glucose sensor of the present embodiment. FIG. 4 is a cross-sectional view of the glucose sensor shown in FIG. 3F, taken along an arrow line I-I, viewed in the arrow direction. In FIGS. 3A to 3F and 4, the same portions are denoted by the same reference numerals.

Figure 3F:
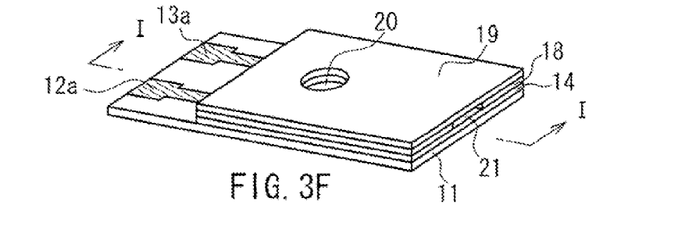
Figure 4:
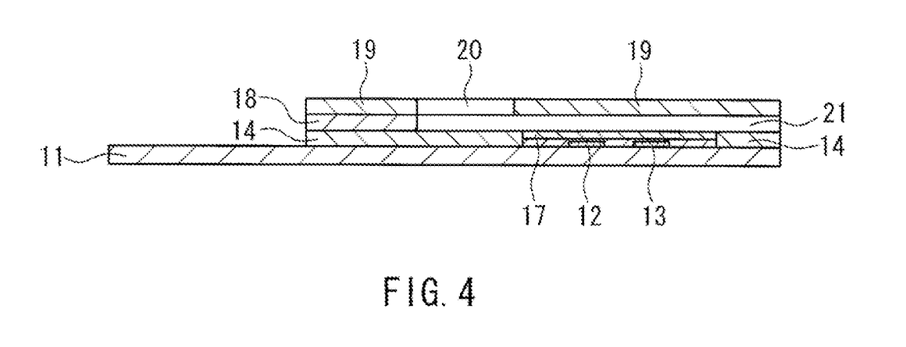
FIG. 4 is a schematic diagram illustrating an exemplary configuration of a glucose sensor.

As shown in FIGS. 3F and 4, this glucose sensor includes a substrate 11; an electrode system composed of a working electrode 12 having a lead part 12a, and a counter electrode 13 having a lead part 13a; an insulative layer 14; an inorganic gel layer 16 containing a layered inorganic compound; an enzyme layer 17 containing *Aspergillus oryzae* type FAD-GDH; a spacer 18 having an opening; and a cover 19 having a through hole 20. It should be noted that a ruthenium compound and PMS are contained separately in at least one of the inorganic gel layer 16 and the enzyme layer 17. The configuration may be such that the inorganic gel layer 16 and the enzyme layer 17 may form one reagent layer, in another embodiment.

As sown in FIG. 3B, a detection section 15 is provided on one end part on one side (on the right side in FIGS. 3 and 4) of the substrate 11, and in the detection section 15, the working electrode 12 and the counter electrode 13 are provided in parallel with each other, along a width direction of the substrate 11. Ends of the electrodes are the lead pans 12a and 13a (on the left side in FIGS. 3 and 4), respectively, which are arranged so as to perpendicularly cross the other end of the detection section 15 (FIG. 3A). A pan between the working electrode 12 and the counter electrode 13 is insulative. On the substrate 11 provided with this electrode system, the institutive layer 14 is laminated, except for areas of the lead parts 12a and 13a and the detection section 15, as shown in FIG. 3B. On the area of the detection section 15, where the insulative layer 14 is not laminated, the inorganic gel layer 16 and the enzyme layer 17 are laminated in this order. On the insulative layer 14, the spacer 18 having an opening corresponding to the detection section 15 is provided, as shown in FIG. 3E. Further on the spacer 18, the cover 19 having the through hole 20 in an area corresponding to a part of the opening is provided (FIG. 3F). In this glucose sensor, an air part that is an air pan of the opening and that is interposed between the enzyme layer 17, the insulative layer 14, and the cover 19 becomes a sample supply section 21 in a capillary structure. The through hole 20 is an air hole for absorbing a sample by a capillary phenomenon.

This glucose sensor can be used in combination with measurement equipment provided with various means, for example, a means for applying a predetermined voltage for a certain set period, a means for measuring electric signals transmitted from the biosensor, a calculation means for calculating the electric signals into a concentration of a measurement object, etc.

An exemplary use of this glucose sensor is explained below.

First, a whole blood sample is brought into contact with an end of the opening 21 of the glucose sensor. As this opening 21 has a capillary structure as described above and the through hole 20 is provided in the cover 19 corresponding to the other end of the opening 21, the sample is sucked into the inside due to the capillary phenomenon. The sample thus sucked permeates into the enzyme layer 17 provided on the detection section 15, dissolves *Aspergillus oryzae* type FAD-GDH in the enzyme layer 17, and reaches a surface of the inorganic gel layer 16 below the enzyme layer 17. Then, reaction occurs among glucose in the sample thus having reached the sulfate, the FAD-GDH, the PMS, and the ruthenium compound. More specifically, the glucose as an object to be measured is oxidized by the FAD-GDH, electrons that migrate due to the oxidation reaction are transformed via the PMS to the ruthenium compound, whereby a reduced type ruthenium (II) complex is formed. Then, electrons are exchanged between the reduced type ruthenium (III) complex that is reduced in the inorganic gel layer 16 and the electrode positioned below the inorganic gel layer 16, whereby a glucose concentration is measured.

[Method for Producing a Glucose Sensor]

The present disclosure, in another aspect, relates to a method for producing a glucose sensor that includes forming a reagent layer containing *Aspergillus oryzae* type FAD-GDH, a ruthenium compound, and PMS on an electrode system having a working, electrode and a counter electrode, the electrode system being provided on an insulative substrate. According to the producing method of the present disclosure, a glucose sensor of the present disclosure can be produced. Configurations and/or contents, etc, of the insulative substrate, the electrode system, and the reagent layer may be made identical to those described above.

[Method for Measuring a Glucose Concentration]

The present disclosure, in another aspect, relates to a method for measuring a glucose concentration in a sample, the method including: bringing the sample in contact with *Aspergillus oryzae* type FAD-GDH; and electrochemically measuring a reaction between the glucose in the sample and the *Aspergillus oryzae* type FAD-GDH via PMS and as ruthenium compound.

In the present specification, "electrochemically measuring" means measurement by applying an electrochemical measuring means, and it is, for example, the amperometric method, the potentiometric method, the coulometric analysis method, or the like, in one or a plurality of embodiments. The amperometric method is, for example, a method of measuring a value of an electric current generated when a reduced electron transfer substance, upon application of a voltage, is oxidized in one or as plurality of embodiments.

An exemplary embodiment of the glucose concentration measurement method according to the present disclosure is as follows: a reaction system including the sample, the *Aspergillus oryzae* type FAD-GDH the PMS and the ruthenium compound is directly provided on an electrode system having a working electrode and a counter electrode provided on an insulative substrate. Alternatively, another embodiment may be as follows: an inorganic gel layer is provided on the electrode system, and a reaction system including the sample and the *Aspergillus oryzae* type FAD-GDH is provided on the inorganic gel layer. In this case, it is preferable that the two types of the mediators exist in at least one of the liquid-phase reaction system and the inorganic gel layer, and it is more preferable that the PMS exists in the reaction system, and the ruthenium compound exists in the inorganic gel layer.

A preferable embodiment of the glucose concentration measurement method of the present disclosure is, for example, a glucose concentration measurement method using the glucose sensor of the present disclosure.

The glucose concentration measurement method of the present disclosure, in another embodiment, may include: applying a voltage to the electrode system after the sample and the *Aspergillus oryzae* type FAD-GDH are brought into contact with each other; measuring as value of a response electric current discharged upon the application of the voltage; and calculating a concentration of glucose in the sample based on the value of the response electric current. The voltage to be applied is not limited particularly, but in one or a plurality of embodiments, it is 10 to 700 mV, 50 to 500 mV or 100 to 400 mV.

In the glucose concentration measurement method of the present disclosure, a voltage may be applied to the electrode system after the electrode system is kept in a state without voltage application for a predetermined period after the sample and the *Aspergillus oryzae* type FAD-GDH are brought into contact, in another embodiment, or alternatively, a voltage may be applied to the electrode system at the same time when they are brought into contact. The period while the electrode system is kept without voltage application is more than 0 second and not more than 30 seconds, or more than 0 second and not more than 10 seconds, in one or a plurality of embodiments.

The application of a voltage to the electrode system, the measurement of the response electric current value, and the calculation of the glucose concentration in the glucose sensor of the present disclosure and the glucose concentration measurement method of the present disclosure can be performed appropriately with use of a conventional glucose concentration measurement device, a glucose concentration measurement device to be developed in future, or the like.

[Glucose Concentration Measurement System]

The present disclosure, in still another aspect, relates to a glucose concentration measurement system for measuring a concentration of glucose in a sample, the system including: the glucose sensor of the present disclosure; a voltage application means for applying a voltage to an electrode system of the glucose sensor; and a measurement means for measuring an electric current in the electrode system.

The voltage application means is not particularly limited as long as it can be conductive with the electrode system of the glucose sensor and can apply a voltage thereto, and a known voltage application means or a voltage application leans be developed in future can be used. In one or a plurality of embodiments, the voltage application means can include a contact that can be in contact with the electrode system of the glucose sensor, a power source such as a direct current power source, and the like.

The measurement means is intended to measure an electric current in the electrode system, generated upon the voltage application, and it may be anything as long as it is capable of measuring a value of a response electric current that is correlated with an amount of electrons discharged from the ruthenium compound in the reagent layer of the glucose sensor, in one or a plurality of embodiments. A measurement means used in a conventional glucose sensor or a glucose sensor to be developed in future can be used.

The following description thither explains the present disclosure, by referring to Examples and Comparative Examples. The interpretation of the present disclosure, however, may not be limited, to the interpretation based on Examples shown below.

EXAMPLE

Example 1 and Reference Example 1

Glucose sensors of Example 1 and Reference Example 1 having the same structure as that shown in FIG. 3F were produced as described below.

First, a PET substrate (length: 50 mm, width: 6 mm, thickness: 250 μm) was prepared as the insulative substrate 11 for a glucose sensor, and a carbon electrode system composed of the working electrode 12 and the counter electrode 13 having lead parts, respectively, was formed on one surface of the insulative substrate 11 by screen printing.

Next, the insulative layer 14 was formed on the electrodes as described below. First, an insulative resin polyester was dissolved in solvent carbitol acetate so as to have a concentration of 75 wt %, whereby an insulative paste was prepared. This insulative paste was applied onto the electrodes by screen printing. The printing conditions were 300 mesh screen and a squeegee of pressure of 40 kg, and an amount of the paste to be printed, was set to 0.002 mL per 1 $cm^2$ of the electrode area. It should be noted that surfaces of the detection section 15, the lead parts 12*a* and 13*a* were not subjected to screen printing. Through a heat treatment at 90° C. for 60 minutes, the insulative layer 14 was formed.

Next, on the detection section 15, on which the insulative layer 14 was not formed, the inorganic gel layer 16 was formed as described below. First, an inorganic gel forming liquid (pH 7.5) was prepared that contains 0.3 wt % of synthetic smectite (trade name: "Lucentite SWN", manufactured by Co-op Chemical Co., Ltd), 6.0 wt % of a ruthenium compound $[Ru(NH_3)]Cl_3$, manufactured by Dojindo Molecular Technologies. Inc.), sodium acetate, and succinic acid. 1.0 μL of this inorganic gel forming liquid was poured onto the detection section 15. It should be noted that the top surface of the detection section 15 had an area of about 0.6 $cm^2$, and the top surfaces of the electrodes 12 and 13 in the detection section 15 had an area of about 0.12 $cm^2$. This was dried at 30° C., whereby the inorganic gel layer 16 was formed.

Further, on the inorganic gel layer 16, the enzyme layer 17 was formed. First, an enzyme liquid containing 2.7 U of *Aspergillus oryzae* type FAD-GDH (trade name: "Glucose dehydrogenase (FAD-dependent) (GLD-351)", manufactured by TOYOBO Co., Ltd.), 25% of 1-methoxy PMS (manufactured by Dojindo Molecular Technologies, Inc.), and ACES (N-(2-Acetamido)-2-aminoethanesulfonic acid) buffering liquid (pH 7.5) was prepared 1.0 μL of this enzyme liquid was poured onto the inorganic gel layer 16 in the detection section 15, dried at 30° C., whereby the enzyme layer 17 was formed.

Finally, the spacer 18 having the opening, was arranged on the insulative layer 14, and further, the cover 19 having the through hole 20, which functions as an air hole, was arranged on the spacer 18, whereby the glucose sensor of Example 1 was produced. As a space of the opening of the spacer 18 interposed between the cover 19 and the insulative layer 14 had a capillary structure, and this space was used as the sample supply section 21.

A glucose sensor of Reference Example 1 was produced in the same manner as that of Example 1 except that the enzyme liquid did not contain 1-methoxy PMS.

Contents of the *Aspergillus oryzae* type FAD-GDH, 1-methoxy PMS, and the ruthenium compound per one glucose sensor of Example 1 were 2.7 U, 500 ppm; and 20 μg, respectively. The unit "U" for the enzyme means an amount of an enzyme that oxidizes 1 μmol of glucose at 37° C. in 1 minute.

Figure 2:
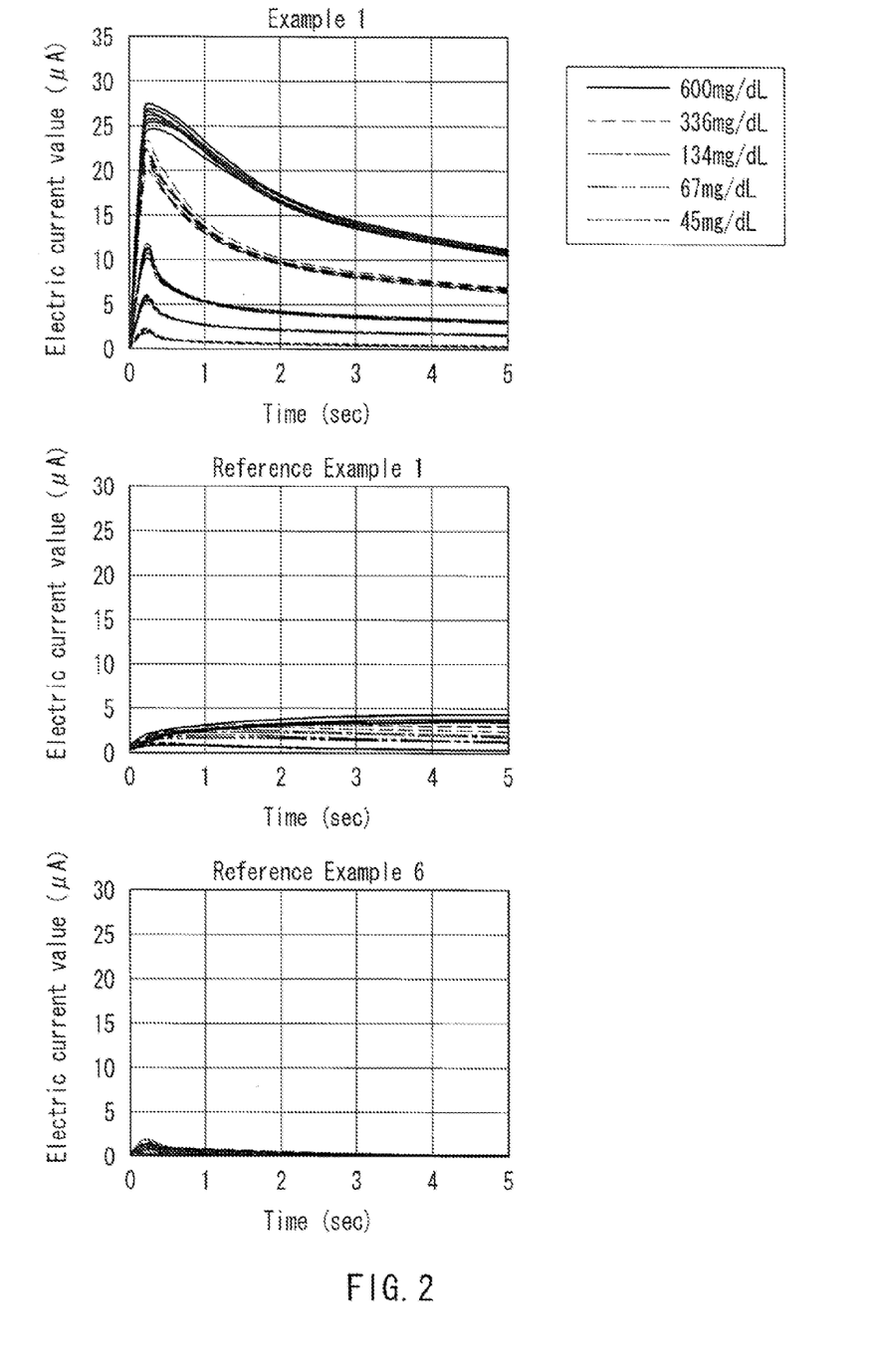
FIG. 2 shows an exemplary graph showing time courses of electric current values detected when samples are measured with glucose sensors of Example 1 and Reference Example 1.

As to the biosensors of Example 1 and Reference Example 1 thus obtained, time courses of electric current values were recorded, which were measured by a blood glucose self-monitoring device (trade name: "GLUCOCARD X-METER", manufactured by ARKRAY Inc.) after the biosensors were caused to react with body samples. The blood glucose self-monitoring device, connected to a performance checker, was capable of accumulating electric current value data. As body samples, samples of venous whole blood having adjusted glucose concentrations (glucose concentration: 45 mg/dL, 67 mg/dL, 134 mg/dL, 336 mg/dL, 600 mg/dL) were used. Obtained time courses are shown in the graphs of FIG. 2. Five types of lines shown in a graph of Example 1 in FIG. 2, from below, indicate results in the cases where the glucose concentration in the sample was 4 mg/dL, 67 mg/dL 134 mg/dL, 136 mg/dL and 600 mg/dL, respectively.

FIG. 2 shows that, since electric currents depending on glucose concentrations in body samples were generated in the glucose sensors of Example 1, it was possible to measure glucose concentrations with the glucose sensors of Example 1. On the other hand, with the glucose sensors of Reference Example 1, it was impossible to measure values of electric currents generated depending on glucose concentrations in body samples; and it was difficult to measure glucose concentrations.

Example 2 and Reference Example 2

Glucose sensors of Example 2 and Reference Example 2 were produced in the same manner as that of Example 1 and Reference Example except that, in place of the *Aspergillus oryzae* type FAD-GDH of Example 1 and Reference Example 1 in which a sugar chain is bound to the non-glycosylated *Aspergillus oryzae* type FAD-GDH (manufactured by TOYOBO Co., Ltd.) in which the sugar chain is not added thereto is used.

Using the produced glucose sensors of Example 2 and Reference Example 2, time courses of electric current values were measured, which were measured after the reaction with body samples of venous whole blood having adjusted glucose concentrations, in the same manner as that of Example 1. As a result, it was found that, with the glucose sensors of Example 2, it was possible to measure glucose concentrations, since electric currents depending on glucose concentrations in the body samples were generated in the glucose sensors of Example 2 (data not shown). On the other hand, it was found that, with the glucose sensors of Reference Example 2, it was impossible to measure values of electric currents generated depending on glucose concentrations in body samples, and it was difficult to measure glucose concentrations (data not shown).

Reference Examples 3 to 7

Glucose sensors of Reference Examples 3 to 7 were produced in the same manner as that of Example 1 except that, in place of 1-methoxy PMS of Example 1, Cytochrome c from *Sacharomyces cerevisiae* (manufactured by Sigma-Aldrich Co. LLC), Cytochrome c from equine heart (manufactured by Sigma-Aldrich Co. LLC), and Cytochrome c from acetylated equine heart (manufactured by Sigma-Aldrich Co. LLC) were used, respectively. Glucose sensors of Reference Example 6 were produced in the same manner as that of Example 1 except that the ruthenium compound was excluded, and glucose sensors of Reference Example 7 were produced in the same manner as that of Example 1 except that the two types of mediators were not contained.

Using the produced glucose sensors of Reference Examples 3 to 5, time courses of electric current values were measured, which were measured alter the reaction with body samples of venous whole blood having adjusted glucose concentrations, in the same manner as that of Example 1. As a result, it was found that, with the glucose sensors of Reference Examples 3 to 6, it was impossible to measure values of electric currents generated depending on glucose concentrations in body samples, and it was difficult to measure glucose concentrations. Exemplary time courses of electric current values measured with the glucose sensors of Reference Example 6 are shown in FIG. 2. With the glucose sensors of Reference Example 7, it was impossible to detect electric current values.

The results of Examples 1 and 2 and Reference Examples 1 to 7 are put together in Table 1 below.

TABLE 1

| | FAD-GDH from *Aspergillus* | Mediator | | Glucose concentration-dependent electric current value |
|---|---|---|---|---|
| Ex. 1 | Glycosylated type | Ruthenium compound | 1-methoxy PMS | Measured (FIG. 2) |
| Ex. 2 | Non-glycosylated type | Ruthenium compound | 1-methoxy PMS | Measured |
| Ref. Ex. 1 | Glycosylated type | Ruthenium compound | — | Not measured (FIG. 2) |
| Ref. Ex. 2 | Non-glycosylated type | Ruthenium compound | — | Not measured |
| Ref. Ex. 3 | Glycosylated type | Ruthenium compound | Cytochrome c from *S. cerevisiae* | Not measured |
| Ref. Ex. 4 | Glycosylated type | Ruthenium compound | Cytochrome c from equine heart | Not measured |
| Ref. Ex. 5 | Glycosylated type | Ruthenium compound | Cytochrome c from acetylated equine heart | Not measured |
| Ref. Ex. 6 | Glycosylated type | — | 1-methoxy PMS | Not measured (FIG. 2) |
| Ref. Ex. 7 | Glycosylated type | — | — | Not measured |

Examples 3 to 6

Glucose sensors of Examples 3 to 6 were produced in the same manner as that of Example 1 except that the contents of 1-methoxy PMS per one glucose sensor were set to 45 ppm, 67 ppm, 134 ppm, and 336 ppm, respectively.

Using the produced glucose sensors of Examples 3 to 6, time courses of electric current values were measured, which were measured after the reaction with body samples of venous whole blood having adjusted glucose concentrations, in the same manner as that of Example 1. As a result it was found that, with the glucose sensors of Examples 3 to 6, it was possible to measure glucose concentrations, since electric currents depending on glucose concentrations in the body samples were generated in the glucose sensors of Examples 3 to 6 (data not shown).

INDUSTRIAL APPLICABILITY

The present disclosure is useful in the medical field, and/or academic fields of medicine, biochemistry, biology, and the like, which are not intended for medical treatments.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A glucose sensor comprising:
   an insulative substrate;
   an electrode system having a working electrode and a counter electrode provided on the substrate; and
   a reagent layer provided on the electrode system,
   wherein the reagent layer contains *Aspergillus oryzae* type flavin adenine dinucleotide dependent glucose dehydrogenase (FAD-GDH), a ruthenium compound, and phenazine methosulfate (PMS).

2. The glucose sensor according to claim 1, wherein the *Aspergillus oryzae* type FAD-GDH is selected from the group consisting of a wild, type FAD-GDH of *Aspergillus oryzae* and modifications of the same, each modification having a sequence obtained, by replacing 1 to 4 amino acid residues in an amino acid sequence of the wild type FAD-GDH and having, a flavin adenine dinucleotide-dependent glucose dehydrogenase activity.

3. The glucose sensor according to claim 1, wherein the PMS is 1-methoxy-5-methylphenazinium methyl sulfate.

4. The glucose sensor according to claim 1, wherein a content of the *Aspergillus oryzae* type FAD-GDH per one glucose sensor is to 4 U, 1 U being an amount of an enzyme that oxidizes 1 μmol of glucose at 37° C. in 1 minute.

5. The glucose sensor according to claim 1, wherein a content of the PMS per one glucose sensor is 100 to 300 pmol.

6. The glucose sensor according to claim 1, wherein a content of the ruthenium compound per one glucose sensor is 15 to 25 μg.

7. A method for measuring, a concentration of glucose in a sample, the method comprising:

bringing the sample and *Aspergillus oryzae* type FAD-GDH into contact with each other; and
   electrochemically measuring a reaction between the glucose in the sample and the *Aspergillus oryzae* type FAD-GDH via PMS and a ruthenium compound.

8. The glucose concentration measurement method according to claim 7, performed with use of the glucose sensor according to claim 1.

9. The glucose concentration measurement method according to claim 8, further comprising:
   applying, a voltage to the electrode system after the contact;
   measuring a value of a response electric current discharged upon the application of the voltage; and
   calculating the glucose concentration in the sample based on the value of the response electric current.

10. A method for producing a glucose sensor, the method comprising forming a reagent layer containing *Aspergillus oryzae* type FAD-GDH, a ruthenium compound, and PMS on an electrode system provided on an insulative substrate, the electrode system having a working electrode and a counter electrode provided on the insulative substrate.

11. A glucose concentration measurement system for measuring a concentration of glucose in a sample, the system comprising:
    the glucose sensor according to claim 1;
    a voltage application device in the glucose sensor; and
    electric current measurement device in the electrode system.

* * * * *

SEQUENCE LISTING

<160> NUMBER OF SEQ ID NOS: 1

<210> SEQ ID NO 1
<211> LENGTH: 572
<212> TYPE: PRT
<213> ORGANISM: Aspergillus oryzae

<400> SEQUENCE: 1

```
Met Lys Asn Thr Thr Thr Tyr Asp Tyr Ile Val Val Gly Gly Thr
 1               5                  10                  15

Ser Gly Leu Val Val Ala Asn Arg Leu Ser Glu Asn Pro Asp Val Ser
                20                  25                  30

Val Leu Leu Leu Glu Ala Gly Ala Ser Val Phe Asn Asn Pro Asp Val
            35                  40                  45

Thr Asn Ala Asn Gly Tyr Gly Leu Ala Phe Gly Ser Ala Ile Asp Trp
        50                  55                  60

Gln Tyr Gln Ser Ile Asn Gln Ser Tyr Ala Gly Gly Lys Gln Gln Val
65                  70                  75                  80

Leu Arg Ala Gly Lys Ala Leu Gly Gly Thr Ser Thr Ile Asn Gly Met
                85                  90                  95

Ala Tyr Thr Arg Ala Glu Asp Val Gln Ile Asp Val Trp Gln Lys Leu
            100                 105                 110

Gly Asn Glu Gly Trp Thr Trp Lys Asp Leu Leu Pro Tyr Tyr Leu Lys
        115                 120                 125

Ser Glu Asn Leu Thr Ala Pro Thr Ser Ser Gln Val Ala Ala Gly Ala
    130                 135                 140

Ala Tyr Asn Pro Ala Val Asn Gly Lys Glu Gly Pro Leu Lys Val Gly
145                 150                 155                 160

Trp Ser Gly Ser Leu Ala Ser Gly Asn Leu Ser Val Ala Leu Asn Arg
                165                 170                 175

Thr Phe Gln Ala Ala Gly Val Pro Trp Val Glu Asp Val Asn Gly Gly
            180                 185                 190

Lys Met Arg Gly Phe Asn Ile Tyr Pro Ser Thr Leu Asp Val Asp Leu
        195                 200                 205

Asn Val Arg Glu Asp Ala Ala Arg Ala Tyr Tyr Phe Pro Tyr Asp Asp
    210                 215                 220

Arg Lys Asn Leu His Leu Leu Glu Asn Thr Thr Ala Asn Arg Leu Phe
225                 230                 235                 240

Trp Lys Asn Gly Ser Ala Glu Glu Ala Ile Ala Asp Gly Val Glu Ile
                245                 250                 255

Thr Ser Ala Asp Gly Lys Val Thr Arg Val His Ala Lys Lys Glu Val
            260                 265                 270

Ile Ile Ser Ala Gly Ala Leu Arg Ser Pro Leu Ile Leu Glu Leu Ser
        275                 280                 285

Gly Val Gly Asn Pro Thr Ile Leu Lys Lys Asn Asn Ile Thr Pro Arg
    290                 295                 300

Val Asp Leu Pro Thr Val Gly Glu Asn Leu Gln Asp Gln Phe Asn Asn
305                 310                 315                 320

Gly Met Ala Gly Glu Gly Tyr Gly Val Leu Ala Gly Ala Ser Thr Val
                325                 330                 335

Thr Tyr Pro Ser Ile Ser Asp Val Phe Gly Asn Glu Thr Asp Ser Ile
            340                 345                 350

Val Ala Ser Leu Arg Ser Gln Leu Ser Asp Tyr Ala Ala Ala Thr Val
        355                 360                 365
```

-continued

```
Lys Val Ser Asn Gly His Met Lys Gln Glu Asp Leu Glu Arg Leu Tyr
    370             375             380

Gln Leu Gln Phe Asp Leu Ile Val Lys Asp Lys Val Pro Ile Ala Glu
385             390             395                         400

Ile Leu Phe His Pro Gly Gly Gly Asn Ala Val Ser Ser Glu Phe Trp
                405             410                 415

Gly Leu Leu Pro Phe Ala Arg Gly Asn Ile His Ile Ser Ser Asn Asp
            420             425                 430

Pro Thr Ala Pro Ala Ala Ile Asn Pro Asn Tyr Phe Met Phe Glu Trp
        435             440                 445

Asp Gly Lys Ser Gln Ala Gly Ile Ala Lys Tyr Ile Arg Lys Ile Leu
        450             455             460

Arg Ser Ala Pro Leu Asn Lys Leu Ile Ala Lys Glu Thr Lys Pro Gly
465             470             475                         480

Leu Ser Glu Ile Pro Ala Thr Ala Ala Asp Glu Lys Trp Val Glu Trp
                485             490                 495

Leu Lys Ala Asn Tyr Arg Ser Asn Phe His Pro Val Gly Thr Ala Ala
            500             505                 510

Met Met Pro Arg Ser Ile Gly Gly Val Val Asp Asn Arg Leu Arg Val
        515             520             525

Tyr Gly Thr Ser Asn Val Arg Val Val Asp Ala Ser Val Leu Pro Phe
        530             535             540

Gln Val Cys Gly His Leu Val Ser Thr Leu Tyr Ala Val Ala Glu Arg
545             550             555                         560

Ala Ser Asp Leu Ile Lys Glu Asp Ala Lys Ser Ala
                565             570
```